United States Patent
Lim et al.

(10) Patent No.: US 10,172,559 B2
(45) Date of Patent: Jan. 8, 2019

(54) IMPLANTABLE DEVICE HEADER WITH EMBEDDED SENSOR AND ANTENNA

(71) Applicant: PACESETTER, INC., Sylmar, CA (US)

(72) Inventors: Wisit Lim, Santa Clarita, CA (US); Reza Imani, Moorpark, CA (US); Brett Villacencio, Valencia, CA (US); Mitch Goodman, Santa Clarita, CA (US); Ofer Rosenzweig, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 54 days.

(21) Appl. No.: 15/154,758

(22) Filed: May 13, 2016

(65) Prior Publication Data
US 2017/0325741 A1    Nov. 16, 2017

(51) Int. Cl.
*A61B 5/00* (2006.01)
*A61B 5/042* (2006.01)

(52) U.S. Cl.
CPC ............ *A61B 5/686* (2013.01); *A61B 5/0031* (2013.01); *A61B 5/042* (2013.01); *A61B 2560/045* (2013.01)

(58) Field of Classification Search
CPC .. A61N 1/375; A61N 1/37512; A61N 1/3754; A61B 5/0031; A61B 5/042; A61B 5/6846; A61B 5/686
See application file for complete search history.

(56) References Cited

U.S. PATENT DOCUMENTS

| | | | |
|---|---|---|---|
| 7,489,968 | B1 | 2/2009 | Alexander et al. |
| 7,729,769 | B1 | 6/2010 | Xie et al. |
| 8,391,983 | B2 | 3/2013 | Lim |
| 9,048,541 | B2 | 6/2015 | Li et al. |
| 2014/0135882 | A1* | 5/2014 | Prasannakumar ... A61N 1/3752 607/116 |
| 2017/0050032 | A1* | 2/2017 | Bogban ................ A61B 5/0008 |

\* cited by examiner

Primary Examiner — Allen Porter, Jr.

(57) ABSTRACT

A device and method for manufacturing an implantable cardiac monitor device are provided. The method joins a feed-through assembly to a device housing having electronic components therein. The feed-through assembly includes conductors having distal ends connected to the electronic components and has proximal ends projecting from the feed-through assembly. The method assembles a header having a sensing electrode and an antenna embedded within a non-conductive header body. The electrode and antenna includes corresponding interconnection plates. The header body includes a housing mounting surface that includes at least one passage aligned with an interconnect cavity that includes the interconnection plates. The header body further includes a window exposing the interconnect cavity and interconnect regions. The method further directs the proximal ends of the conductors through the passage to align with the interconnect regions and secures the proximal ends and the interconnect regions to one another through the window.

8 Claims, 11 Drawing Sheets

IMPLANTABLE DEVICE HEADER WITH EMBEDDED SENSOR AND ANTENNA

BACKGROUND OF THE INVENTION

Embodiments herein generally relate to implantable cardiac monitoring devices, and more particularly to implantable cardiac monitoring devices with headers having embedded components.

An implantable cardiac monitoring (ICM) device is a medical device that is implanted in a patient to, among other things, monitor electrical activity of a heart. An ICM device may record cardiac activity of a patient over time and report such cardiac activity to an external device. The ICM device may optionally perform various levels of sophisticated analysis of the cardiac activity and based thereon perform additional recording operations. The ICM device may also be configured to deliver appropriate electrical and/or drug therapy, and as such is also referred to as an implantable medical device (IMD). Examples of IMDs include pacemakers, cardioverters, cardiac rhythm management devices, defibrillators, and the like. The electrical therapy produced by an IMD may include, for example, pacing pulses, cardioverting pulses, and/or defibrillator pulses. The device is used to both provide treatment for the patient and to inform the patient and medical personnel of the physiologic condition of the patient and the status of the treatment.

In general, an ICM include a battery, memory and electronic circuitry that are hermetically sealed within a metal housing (generally referred to as the "can"). The metal housing typically is formed of titanium and includes a shell (e.g., opposed concave half shells that are welded together, a "deep drawn shell, etc.) to form a device housing with an interconnect cavity, in which the battery, memory, pulse generator and/or processor module reside. The half shells have an oval contour with a header receptacle area configured to receive a header assembly. A feed-through assembly is located at the header receptacle area and is sealed to the device housing to form an interface for conductors to enter/exit the interconnect cavity.

However, ICM devices and methods of manufacture have experienced certain limitations. Certain types of ICM devices include one or more sensing electrodes and an antenna that are located within the ICM device. For example, the sensing electrode/electrodes and antenna may be located in the header of the ICM device. Heretofore, the sensing electrodes and antenna were joined to the device in a manner that required extensive secondary operations for buffering, sanding and cleaning the header and the device during assembly.

A need remains for improved ICM devices and methods of manufacture.

SUMMARY

In accordance with embodiments herein a method is provided for manufacturing an implantable cardiac monitor device comprising assembling a device housing having electronic components therein. The method joins a feed-through assembly to the device housing. The feed-through assembly includes conductors having distal ends connected to the electronic components and has proximal ends projecting from the feed-through assembly. The method assembles a header having a sensing electrode and an antenna embedded within a non-conductive header body. The electrode and antenna includes corresponding interconnection plates. The header body includes a housing mounting surface that includes at least one passage aligned with an interconnect cavity that includes the interconnection plates. The header body further includes a window exposing the interconnect cavity and interconnect regions. The method further directs the proximal ends of the conductors through the passage to align with the interconnect regions and secures the proximal ends and the interconnect regions to one another through the window.

Optionally, the assembling operation may comprise injection molding a flowable material about the electrode and antenna. The assembling operation may comprise casting a flowable material about the electrode and antenna. The method may further comprise configuring the electronic components to record cardiac signals sensed by the sensing electrode. The header may be molded or cast to embed the electrode and antenna in a header body before securing the header to the device housing. The header may include opposite sides that are elongated to extend along a longitudinal axis and the electrode includes a body portion. The assembling operation may comprise positioning the body portion to face laterally proximate to a side of the header and to orient the body portion along a plane that extends at a select angle to the longitudinal axis.

Optionally, the passage may extend in a first direction from the mounting surface through the header and the window opens laterally onto a side of the header. The header body may include an interconnect cavity having at least one passage extending thereto from a mounting surface. The mounting surface may be configured to adjoin the device housing. The header body may include a window provided in a side of the header body, the window affording access to the interconnect cavity. The securing operation may include welding the proximal ends of the conductors to the corresponding interconnect regions of the sensor and antenna. The method may further comprise injecting an adhesive or epoxy through the window such that the adhesive or epoxy flows through the window and into the interconnect cavity and the passages. The header body may include a mounting surface having a recessed chamber therein, the recessed chamber configured to receive a feedthrough assembly on the device housing.

In accordance with embodiments herein an implantable cardiac monitor device is provided comprising a device housing having electronic components therein. The implantable cardiac monitor device further comprises a feed-through assembly joined to the device housing. The feed-through assembly includes conductors having distal ends connected to the electronic components and has proximal ends projecting from the feed-through assembly. A header is provided having a header body with a sensing electrode and an antenna embedded therein. The electrode and antenna include corresponding interconnect regions. The header body includes a housing mounting surface that includes at least one passage aligned with the interconnection regions. The header body further including a window exposing the interconnect regions. The proximal ends of the conductors extend through the passage and aligning with the interconnection regions. The windows are configured to provide access to the proximal ends and the interconnection regions.

Optionally, the header body may be formed of an injection molded flowable material that embeds the electrode and antenna therein. The header body may include a recessed chamber formed in the housing mounting surface. The header body may further comprise a band provided about a perimeter of the recessed chamber. The band may include one or more tabs that are bent to extend inward above the recessed chamber to provide mechanical anchoring points between the header and the device housing. The electronic components may be configured to record cardiac signals sensed by the sensing electrode.

Optionally, the header may be molded or cast to embed the electrode and antenna in the header body. The header may include opposite skies that may be elongated to extend along a longitudinal axis and the electrode may include a sensor body portion. The sensor body portion may be positioned to face laterally proximate to one of the skies of the header. The sensor body portion may be oriented along a plane that extends at a select angle relative to the longitudinal axis. The passage may extend in a first direction from the mounting surface through the header and the window may open laterally onto a side of the header. The header body may include an interconnect cavity having at least one passage extending thereto from a mounting surface. The mounting surface may be configured to adjoin the device housing. The header body may include a window provided in a side of the header body. The window may afford access to the interconnect cavity.

DETAILED DESCRIPTION

In accordance with embodiments herein, methods and devices are described that afford a high precision process suitable for manufacturing small form factor implantable cardiac monitoring (ICM) devices (including implantable medical devices configured to deliver therapies). The methods and devices described herein provide increased manufacturing output as compared to conventional manufacturing techniques and eliminate numerous conventional manufacturing operations, such as buffering, sanding and cleaning of headers and devices during assembly.

Figure 1:
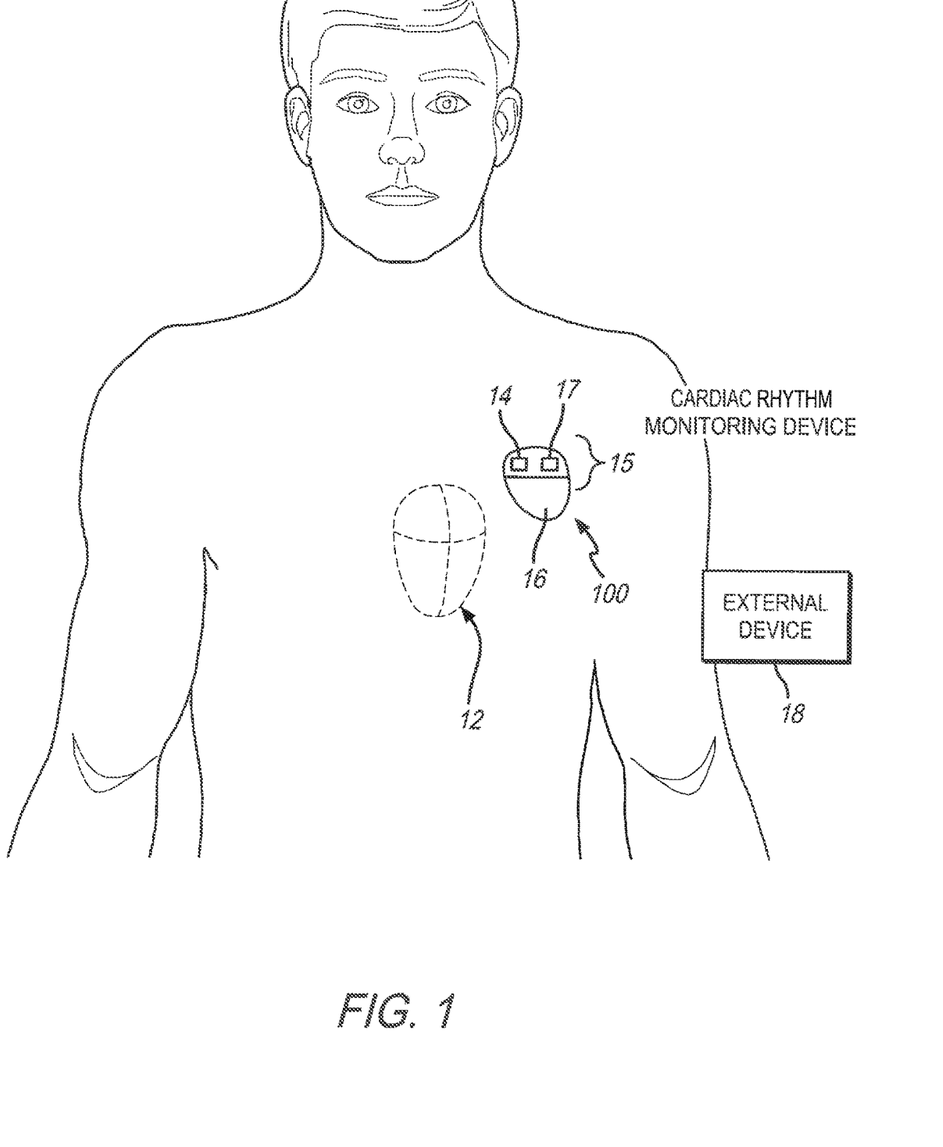
FIG. 1 illustrates an implantable cardiac monitoring (ICM) device intended for subcutaneous implantation at a site near the heart in accordance with embodiments herein.

FIG. 1 illustrates an implantable cardiac monitoring (ICM) device 100 intended for subcutaneous implantation at a site near the heart 12. The ICM 100 includes a housing 16 that is joined to a header 15. At least one electrode 14 is provided in the header 15 and is electrically isolated from the housing 16. The header 15 also includes at least one antenna 17. Optionally, the ICM device 100 may include multiple sensing electrodes 14 positioned in the header and/or on the housing 16. The electrodes 14 may be located in various locations on the housing 16. For example, when separate housing portions are provide for the electronic components and the battery, one or more electrodes may be located on the housing portion that holds the battery (e.g., the battery housing). The sense electrode 14 is provided for detection of far field electrogram signals. Numerous configurations of electrode arrangements are possible.

The housing 16 includes various other components such as sense electronics for receiving signals from the electrodes, a microprocessor for processing the signals in accordance with algorithms (e.g., an AF detection algorithm), a memory for temporary storage of electrograms, a device memory for long-term storage of electrograms upon certain triggering events, such as AF detection, sensors for detecting patient activity and a battery for powering components.

The ICM device 100 senses far field, subcutaneous electrograms, processes the electrograms to detect arrhythmias and automatically records the electrograms in memory for subsequent transmission through the antenna 17 to an external device 18. Electrogram processing and arrhythmia detection is provided for, at least in part, by algorithms embodied in the microprocessor. In one configuration, the monitoring device is operative to detect atrial fibrillation.

Figure 2A:
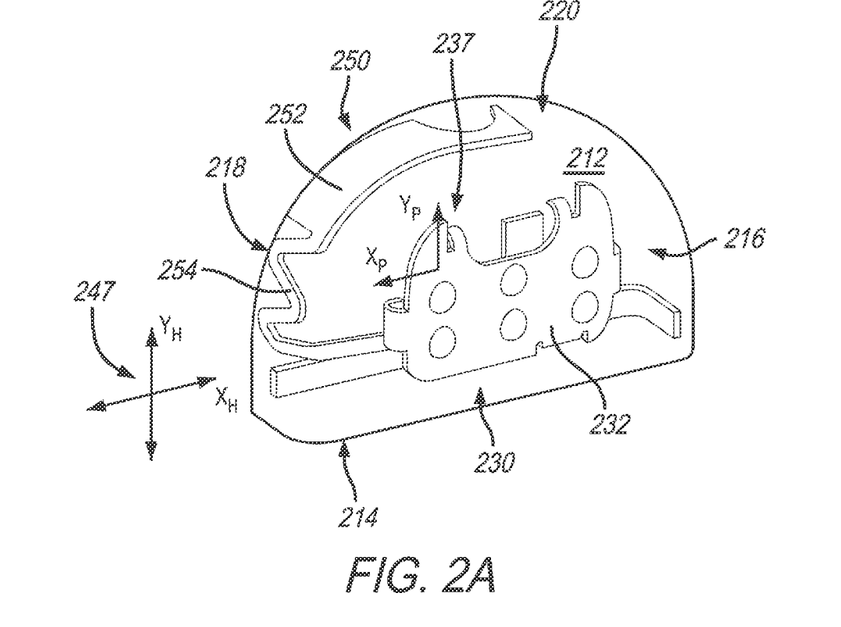
FIG. 2A illustrates a side perspective view of a header to be assembled with the implantable cardiac monitoring device in accordance with embodiments herein.

FIG. 2A illustrates a side perspective view of a header 210 (corresponding to header 15) to be assembled with the implantable cardiac monitoring device 100 in accordance with embodiments herein. The header 210 includes a header body 212 that is formed in a semicircular or half-moon shape with a housing mounting surface 214, opposed sides 216, 218, ends 222 and a curved outer or distal surface 220. The ends 222, distal surface 220 and opposed sides 216, 218 merge with one another along smooth beveled regions to form a smooth overall contour for the body 212. The opposite sides 216, 218 are shaped to extend along a longitudinal axis (designated by arrow $X_H$). The header body 212 is elongated along a header plane (as designated by arrows $X_H$ and $Y_H$).

Figure 2B:
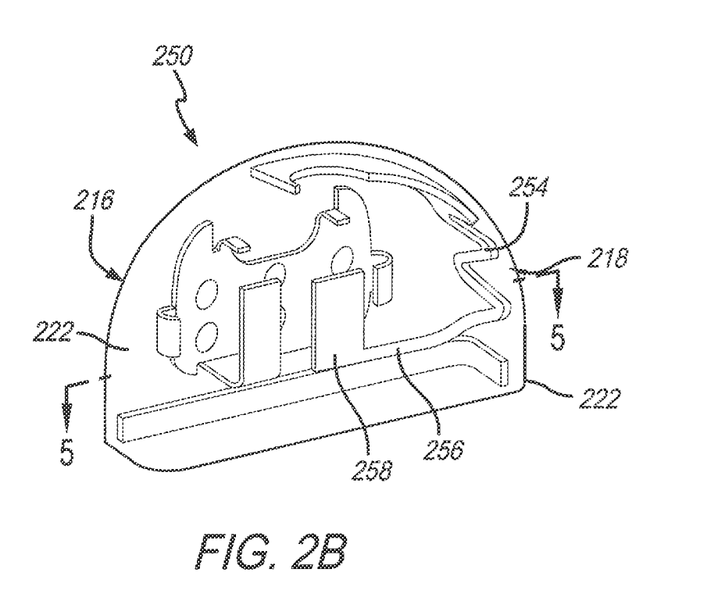
FIG. 2B illustrates a side perspective view of the header from a side opposite to the perspective of FIG. 2A in accordance with embodiments herein.

FIG. 2B illustrates a side perspective view of the header 210 from a side opposite to the perspective of FIG. 2A. In FIG. 2B, the side 218 is exposed, while the side 216 is not visible. In FIGS. 2A and 2B, the body 212 is illustrated in a partially transparent manner in order to illustrate internal structures within the header 210. As explained herein, the header 210 includes, among other things, at least one sensing electrode 230 and at least one antenna 250. The sensing electrode 230 and antenna 250 may be constructed in various shapes, oriented in different manners and positioned in different locations within the header body 212.

Figure 3:
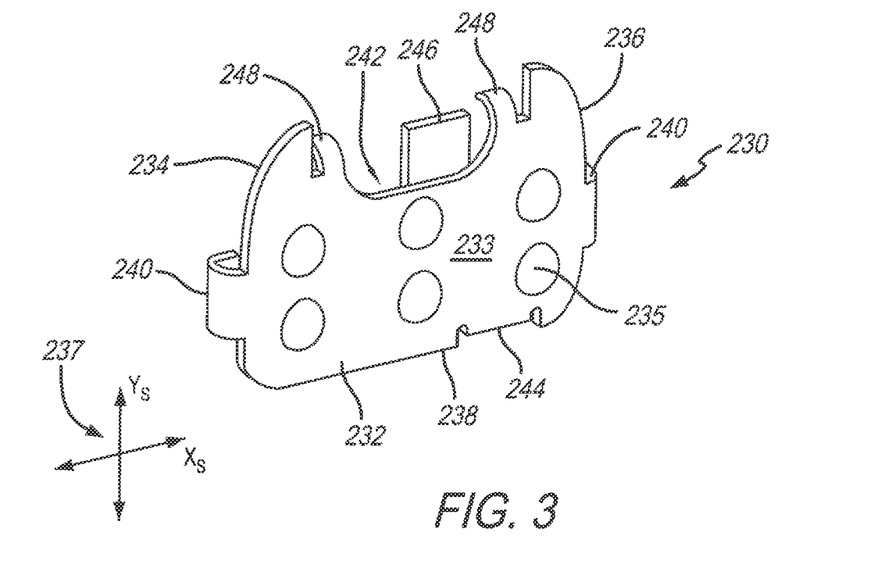
FIG. 3 illustrates a side perspective view of a sensing electrode formed in accordance with an embodiment herein.

FIG. 3 illustrates a side perspective view of a sensing electrode 230 formed in accordance with an embodiment herein. The sensing electrode 230 is shaped to include a planar sensor body portion 232 having end edges 234, 236 and a bottom edge 238. The sensor body portion 232 of the sensing electrode 230 is oriented along a sensor plane (as designated by arrows $X_S$ and $Y_S$). A leg segment 244 extends in a direction transverse from the sensor body portion 232 and is joined to a sensor interconnect region 246. The interconnect region 246 is aligned with, and transversely spaced apart from, the sensor body portion 232. The edges 234, 236 include lateral clips 240 provided thereon and bent toward the interconnect region 246 and a rear face 242 of the sensor body 232. Top clips 248 are also provided along an upper edge of the sensor body 232 and bent toward the interconnect region 246 in a direction of the rear face 242.

In the example of FIG. 3, a front face 233 of the sensor body portion 232 includes a series of raised detents 235 extending outward therefrom and arranged in a pattern (e.g. a two-dimensional array). Optionally, the detents 235 may be omitted, or more or fewer detents may be used. In the present example, the electrode body 232 is formed in a generally rectangular shape, however alternative shapes may be utilized.

Returning to FIGS. 2A and 2B, the sensing electrode 230 is positioned such that the planar body portion 232 faces laterally and is located proximate to one side (e.g. side 216) of the header body 212. The body portion 232 is oriented such that the sensor plane 237 (as designated by arrows $X_S$ and $Y_S$) is oriented at a select angle with respect to a header plane 247 (as designated by arrows $X_H$ and $Y_H$). For example, the sensor plane 237 may extend in a common direction (e.g. parallel) as the header plane 247.

Figure 4:
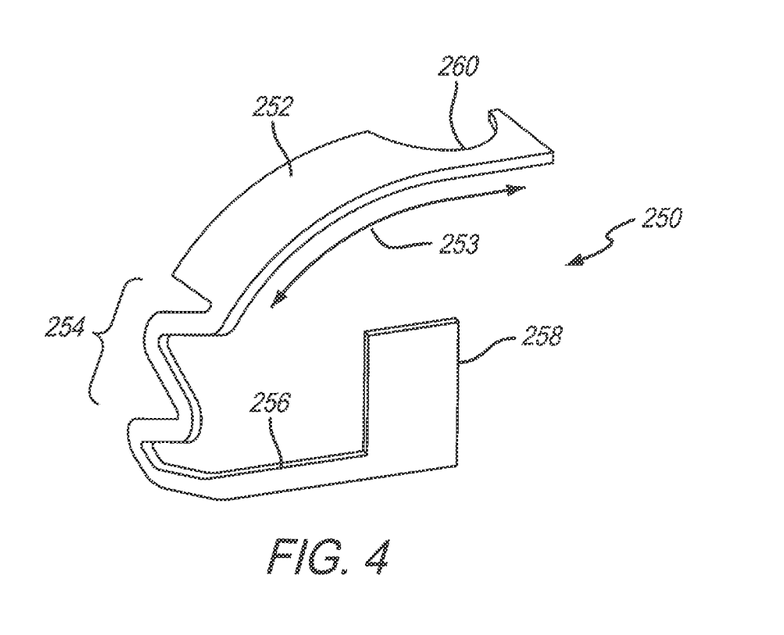
FIG. 4 illustrates a side perspective view of an antenna formed in accordance with an embodiment herein.

FIG. 4 illustrates a side perspective view of an antenna 250 formed in accordance with an embodiment herein. By way of example only, the antenna 250 may be constructed to support communications in accordance with a Bluetooth protocol, a Wi-Fi protocol, or various other wireless protocols. The antenna 250 includes an antenna substructure 252 that is located proximate to a distal end of the antenna 250. The antenna substructure 252 is formed in a generally rectangular shape bent along an arcuate path 253 that substantially conforms to the shape of the outer distal surface 220 (FIG. 2A) of the header body 212. The antenna substructure 252 includes a semicircular notched out portion 260, although alternative shapes may be utilized for the antenna substructure 252 based upon the particular design constraints and wireless protocol. The antenna substructure 252 is joined to an intermediate branch 254 that extends in a curved or serpentine manner. The intermediate branch 254 is joined to a base stem 256 that is in turn coupled to an antenna interconnect region 258.

With reference to FIGS. 2A and 2B, the antenna substructure 252 is located proximate to, and extends along, the outer distal surface 220 of the header body 212. The intermediate branch 254 also extends along an end portion 222 of the header body 212 until joining the base stem 256 that extends into an interconnect cavity of the header body 212 away from the end portion 222. The base stem 256 joins the interconnect region 250 that is located in the interconnect cavity of the header body 212 proximate to the housing mounting surface 214. The interconnect region 258 is oriented to extend in a common direction, but is spaced apart from, the body portion 232 of the sensing electrode 230.

Figure 5:
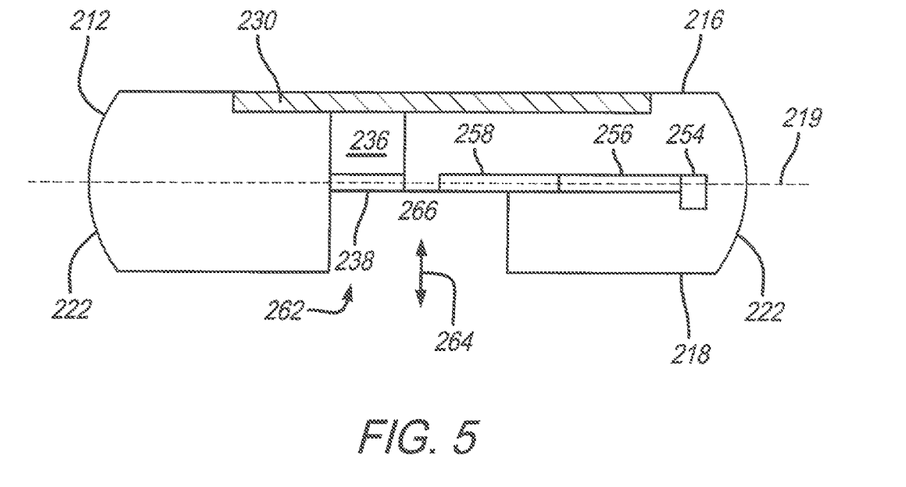
FIG. 5 illustrates a top sectional view of the header taken along line 5-5 in FIG. 2B in accordance with embodiments herein.
Figure 6:
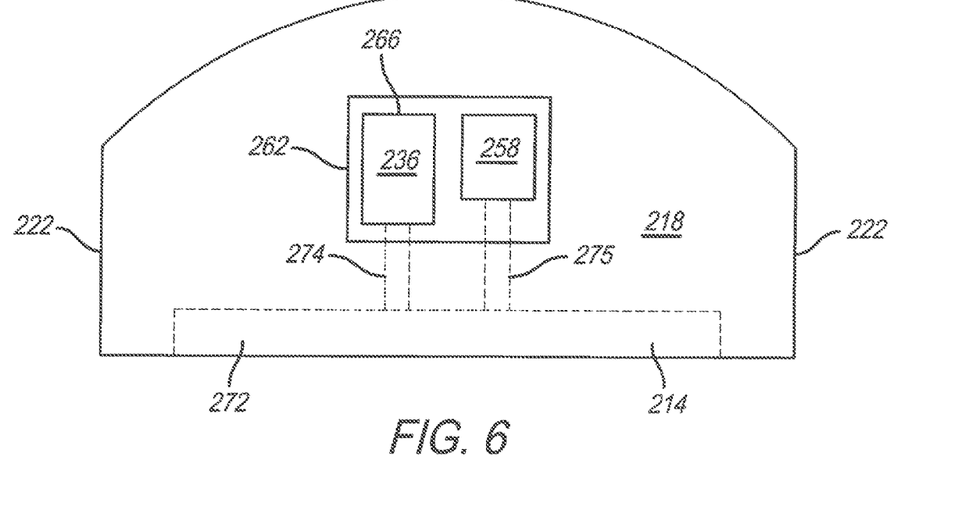
FIG. 6 illustrates a front plan view of the header in accordance with embodiments herein.

FIG. 5 illustrates a top sectional view of the header 210 taken along line 5-5 in FIG. 2B, while FIG. 6 illustrates a front plan view of the header 210. For purposes of simplification, various structures embedded within the header body 212 are not illustrated in FIGS. 5 and 6. The top sectional view of FIG. 5 better illustrates the sides 216, 218 and end portions 222 of the header body 212. The header body 212 encapsulates/embeds the antenna 250, from which the intermediate branch 254, and base stem 256 are illustrated in FIG. 5. The header body 212 also encapsulates/embeds the sensing electrode 230. The header body 212 is elongated along a longitudinal axis 219. At least one of the skies 218, 216 includes a window 262 that is oriented in a transverse direction (as denoted by arrow 264) relative to the axis 219. The window 262 opens onto an interconnect cavity 266. The electrode and antenna interconnect regions 238 and 258 are located within the interconnect cavity 266. The antenna interconnect region 258 is joined to the base stem 256 that is embedded within the header body 212. The electrode interconnect region 238 is joined to the sensor body portion 232 through an electrode stem 236 which is embedded within the header body 212. The window 264 and cavity 266 afford access to the interconnect regions 238, 258 during a welding assembly operation.

In FIG. 6, the window 262 is shown more clearly from a side view perspective. The window 262 is generally located in an intermediate region of the header body 212 and spaced apart from the mounting surface 214, end portions 222 and distal surface 220. As shown in FIG. 6, the sensor interconnect region 238 and antenna interconnect region 258 are visible and accessible through the window 262. In the example of FIG. 6, the interconnect regions 238, 258 are generally rectangular, however, alternative shapes may be utilized.

A recessed chamber 272 is provided at the housing mounting surface 214. The recessed chamber is 272 shaped and dimensioned to receive a feed-through assembly on the device housing during assembly. In the present example, the recessed chamber 272 is rectangular in shape, although alternative shapes may be used based on the shape of the feed through housing. One or more passages 274, 275 extend between the recessed chamber 272 and the interconnect cavity 266. For example, the passages 274, 275 may be shaped to receive corresponding individual conductors that pass through the feed through assembly. The passages 274, 275 align with the interconnect regions 238, 258 such that, when the conductors are inserted through the passages 274, 275 from the recessed chamber 272 toward the interconnect cavity 266, the conductors align with the corresponding interconnect regions 238, 258.

Next, a process of manufacturing a header and ICM device in accordance with embodiments herein is described.

Figure 7A:
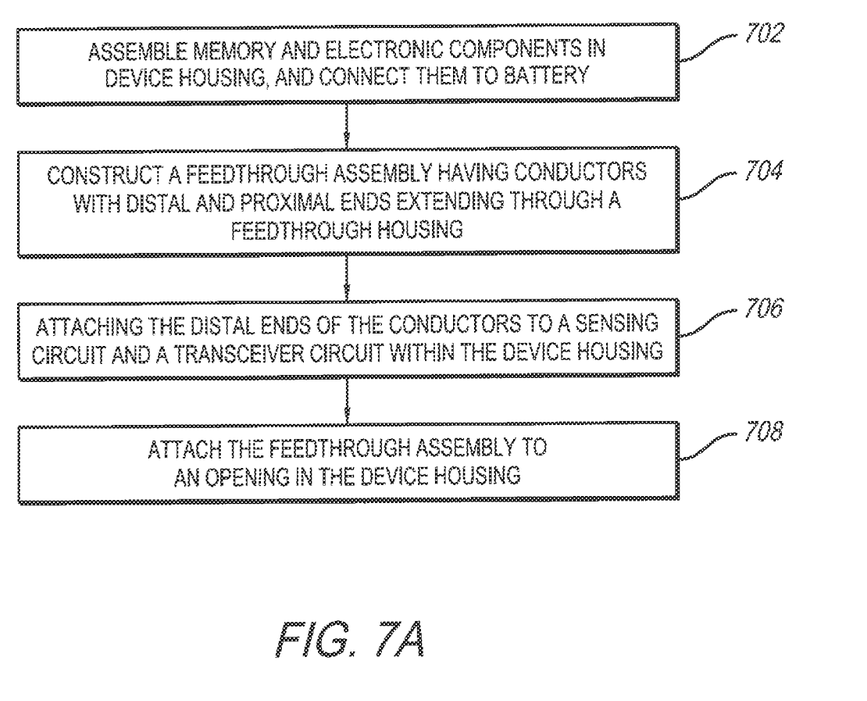
FIG. 7A illustrates a process for manufacturing an implantable cardiac monitoring device in accordance with embodiments herein.
Figure 7B:
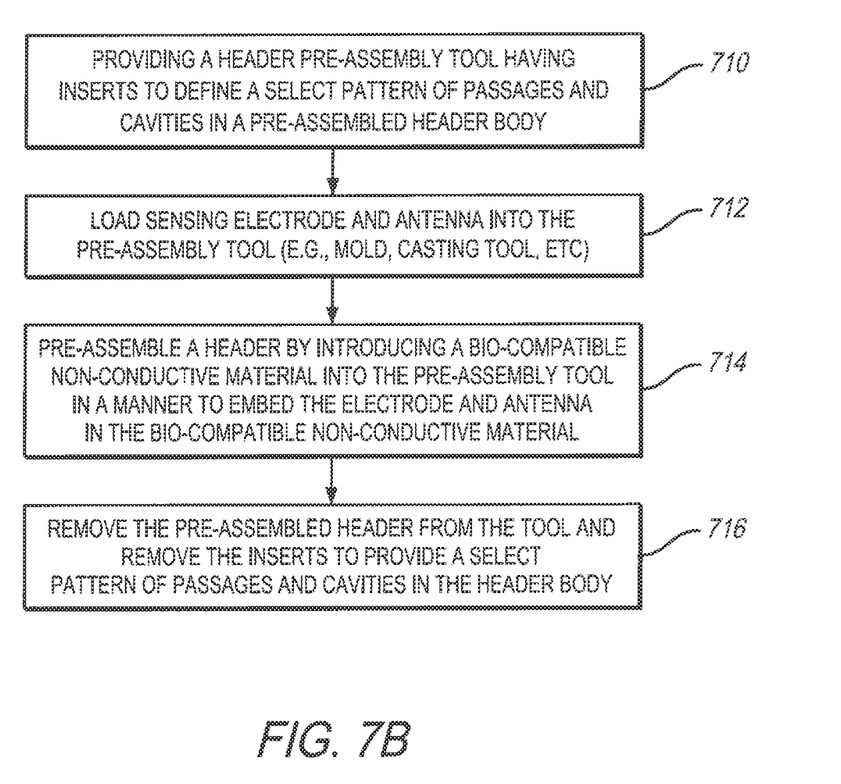
FIG. 7B illustrates the process for pre-assembling a header in accordance with embodiments herein.
Figure 7C:
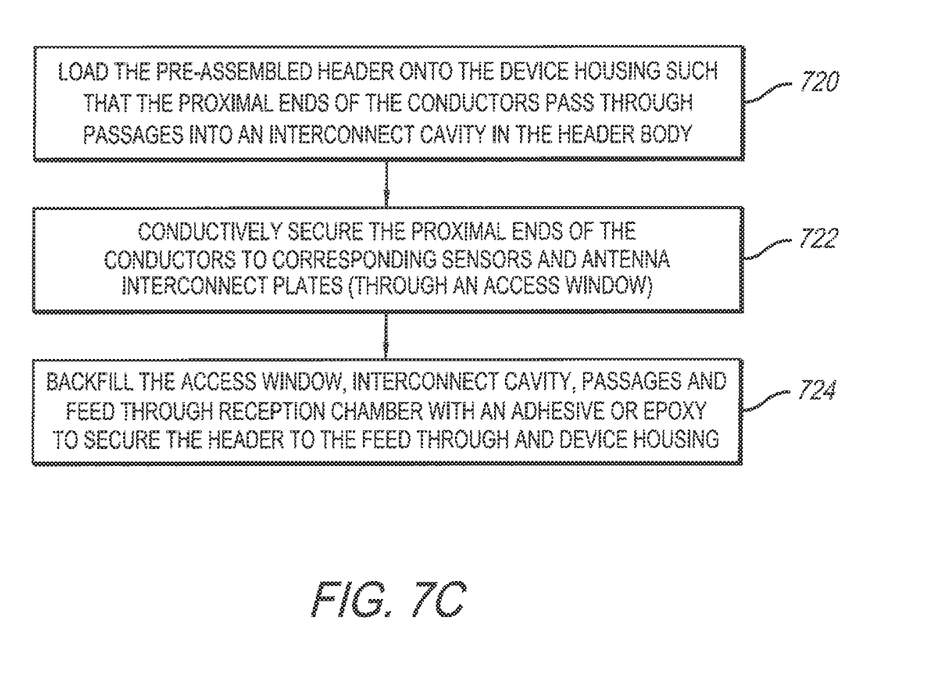
FIG. 7C illustrates a process for combining the header and the ICM/IMD device housing in accordance with embodiments herein.

FIGS. 7A-7C illustrate a process for manufacturing an implantable cardiac monitoring device in accordance with embodiments herein. At 702, the process includes assembling memory and electronic components in a device housing, and attaching a battery to an open end of the housing. Examples of the various electronic components are described herein. The electronic components may include sensing circuitry to sense cardiac signals of interest, one or more processors to perform monitoring operations, transceiver circuitry to communicate with external devices and other components as described herein and/or understood by one of ordinary skill in the art. The memory, processors and other electronic components are positioned within a housing formed of a biocompatible material. The housing includes a feedthrough opening at one end and a battery attachment surface at an opposite end. A hermetically sealed battery is welded to the battery attachment surface, and a feedthrough is welded to the feedthrough opening, thereby hermetically sealing the interior of the housing.

Figure 7D:
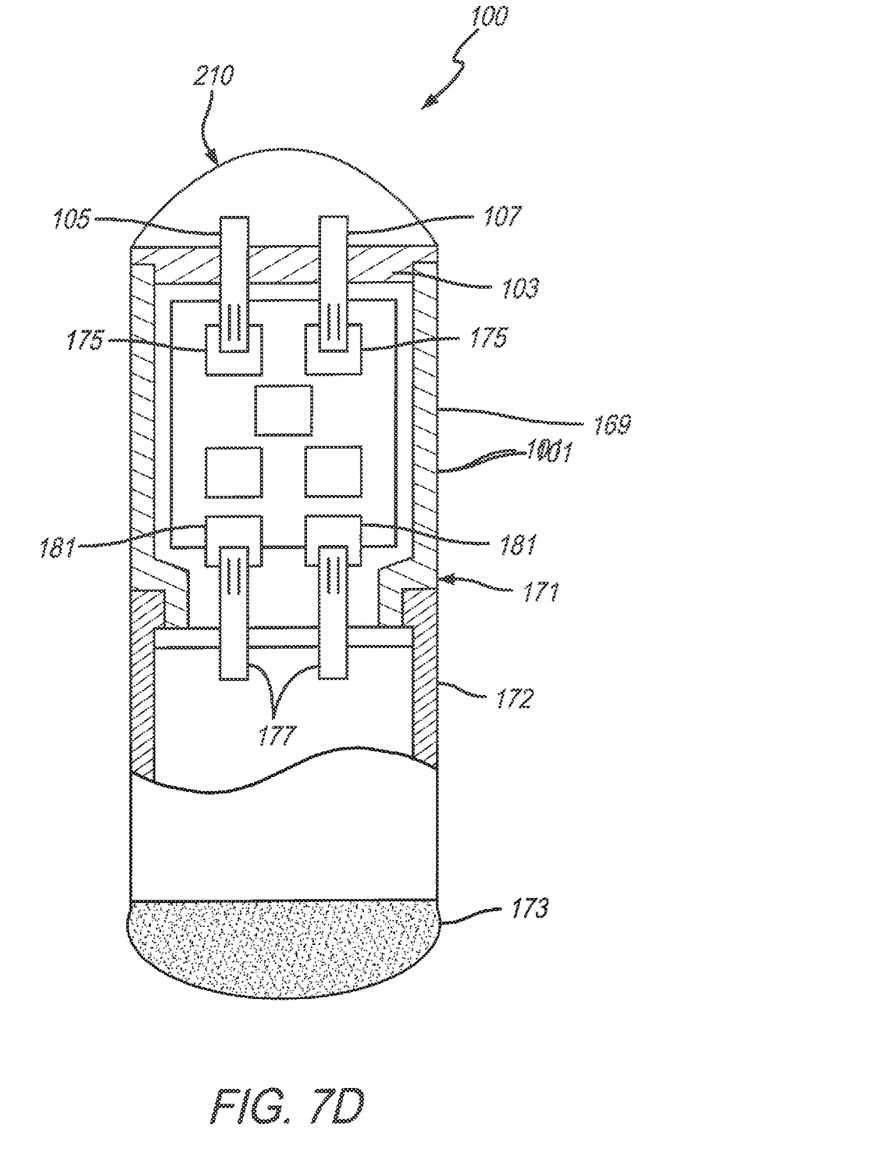
FIG. 7D illustrates a cross-sectional view of an ICM device 100 formed in accordance with an embodiment herein.

FIG. 7D illustrates a cross-sectional view of an ICM device 100 formed in accordance with an embodiment herein. The ICM device 100 includes the header 210 attached to one end of the housing 101, while the opposite end of the housing 101 is connected to a battery 172. An electrode 173 is provided on an exterior surface of the battery 172. Pins 177 connect the battery 172 to pads 181 on the board 169. By way of example, an open end 171 of the housing 101 is tapered to fit within an opening in an end of the battery 172, with an interface there between welded to form a seal. The housing 101 encloses memory and electronics on one or more circuit boards 169 that are coupled to conductors 105, 107. The conductors 105, 107 extend through the feedthrough housing 103 and attach to pads 175 on the board 169. A ground connection is also maintained between the feed through the housing 103 and the circuit board 169. It is understood that the example of FIG. 7D represents one exemplary construction, while ICM devices may be constructed with numerous alternative shapes and combinations of components therein.

At 704, a feedthrough assembly is constructed that includes one or more conductors that extend through a feedthrough housing. For example, the conductors may include one or more conductors intended to convey sensing signals between one or more sensing electrodes in the header and sensing circuitry within the device housing. The conductors may also include one or more conductors configured to convey communications signals and data between one or more antenna within the header and communications/transceiver circuitry within the device housing. The conductors include proximal and distal ends, with the distal ends being located within the device housing and electrically coupled to the corresponding sensing and transceiver circuitry. The proximal ends extend from the feedthrough housing to locations outside/exterior to the device housing.

At 706, the distal ends of the conductors are attached to corresponding sensing circuitry and the transceiver/communications circuitry within the device housing. At 708, the feedthrough assembly is inserted in the opening in the device housing and sealed thereto to hermetically seal the interconnect cavity within the device housing.

FIG. 7B illustrates the process for pre-assembling a header in accordance with embodiments herein. At 710, a header pre-assembly tool is prepared, such as by including inserts into the tool that define a select pattern of passages and cavities to be created within the header body once the pre-assembly process is complete. For example, the inserts may be permanently affixed within the pre-assembly tool at the time the tool is manufactured. Optionally, the inserts may be movable and replaceable at the time a collection of headers are to be pre-assembled. By way of example, the tool may represent a mold, casting tool and the like.

At 712, one or more sensing electrodes and one or more antenna are loaded into the preassembly tool. The electrode and antenna may be held in the tool in various manners.

At 714, a biocompatible nonconductive flowable material is introduced into the preassembly tool in a manner to embed the one or more sensing electrodes and one or more antenna within the biocompatible nonconductive material. The flowable material may represent various types of flowable injection molding materials, such as Tecothan® aromatic polyether-based thermoplastic polyurethanes (TPUs) (as offered by the Lubrizol Corporation). Optionally, the non-conductive flowable material may be a Bionate® polymer (e.g., as offered by DSM Biomedical Corporation) or another thermoplastic polycarbonate urethane (PCU) polymers. Optionally, the non-conductive flowable material may represent a pre-casting type of material, such as epoxy and the like. The flowable material is introduced at a desired viscosity and temperature and under a desired pressure and other predetermined conditions such that the flowable material encases the electrode and antenna without any voids therein.

At 716, the pre-assembled header is removed from the tool after the non-conductive material has solidified by a desired amount. The inserts and tool are separated with the header body includes the sensor and antenna embedded/encased therein. The header body also includes a pattern of passages, cavities, chambers and the like as defined by the inserts within the preassembly tool. The preassembly process of FIG. 7B may be completed at an entirely separate location (e.g. a supplier facility) and at an entirely separate time as the remainder of the operations of FIGS. 7A and 7C. The preassembly process of FIG. 7B eliminates and avoids any need for traditional preassembly processes, such as conventional sanding, buffering and cleaning processes.

FIG. 7C illustrates a process for combining the header and the ICM/IMD device housing. At 720, the preassembled header is loaded onto the device housing. The proximal ends of the conductors (that extend from the feedthrough assembly) are received within, and pass through, passages within the header body until extending into an interconnect cavity within the header body.

Figure 8A:
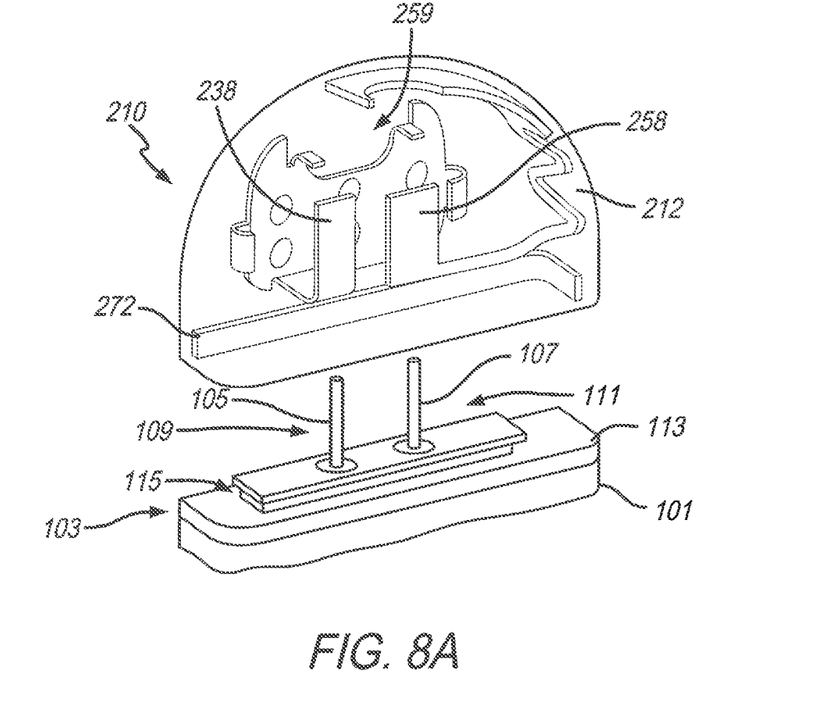
FIG. 8A illustrates a side perspective view of the header being loaded onto a device housing in accordance with embodiments herein.

FIG. 8A illustrates a side perspective view of the header 210 while being loaded onto a device housing 101. A feedthrough housing 103 has been hermetically sealed to an opening in the device housing 101, while proximal ends 105, 107 of conductors 109, 111 extend through the feedthrough housing 103. In the example of FIG. 8, the feedthrough housing 103 includes a base 113 that is joined to a standoff portion 115. As explained herein, a recessed chamber 272 is provided in the header body 212 and positioned to open on to the housing mounting surface 214. The proximal ends 105, 107 of the conductors 109, 111 are aligned to pass through passages until being positioned proximate to the sensor and antenna interconnect regions 238, 258, respectively.

Figure 8B:
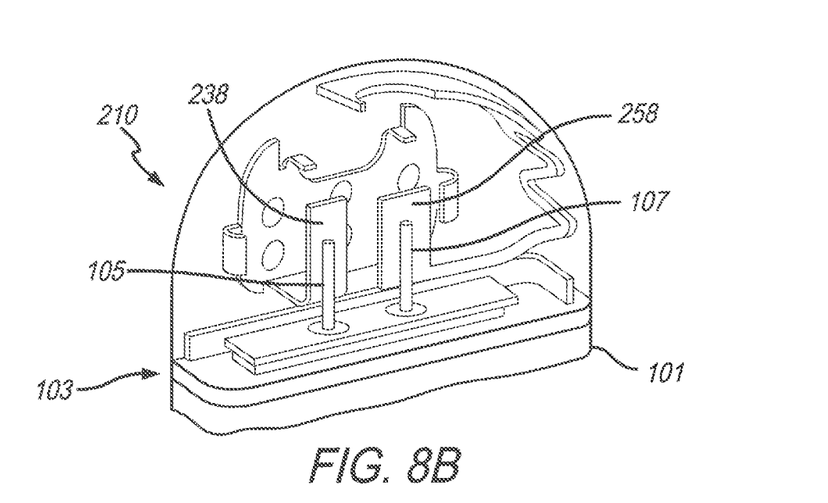
FIG. 8B illustrates the header when fully seated on to the housing and feedthrough assembly in accordance with embodiments herein.

FIG. 8B illustrates the header 210 when fully seated on to the housing 101 and feedthrough assembly 103. As shown in FIG. 8B, the proximal portions 105, 107 are aligned substantially adjacent and extend along the interconnect regions 238, 258. While not visible in FIG. 8B, the window 262 (FIG. 5) is aligned with the proximal portions 105, 107 and interconnect regions 238, 258 to afford an interconnection operation.

Optionally, the header 210 may include a suture through hole 259 that remains open after manufacture. The suture through hole 259 may receive a suture at the time of implant to secure the device at a desired implant location when implanted. The suture through hole is defined by one or more inserts that are provided within the preassembly tool.

Returning to FIG. 7C, at 722, the proximal ends 105, 107 of the conductors 109, 111 are conductively secured to the corresponding sensor and antenna interconnect regions 238, 258. For example, the securing operation may include welding the conductors 109, 111 to the corresponding interconnect regions 238, 258. The window 262 in the header body 212 affords access to the proximal ends 105, 107 of the conductors 109, 111 and the interconnect regions 238, 268 during the welding operation.

At 724, a medical adhesive or epoxy is injected into the passages and cavities within the header body. For example, the adhesive or epoxy may be injected through the window 262 with sufficient pressure to force the adhesive or epoxy to fill the interconnect cavity 266, passages 274, 275 and feedthrough reception chamber 272. The adhesive or epoxy fills any open passages or voids within the header body 212 including the interface between the feedthrough reception chamber 272 and the device housing 101 and feedthrough housing 103, in order to secure the header to the feedthrough and device housing.

Figure 9:
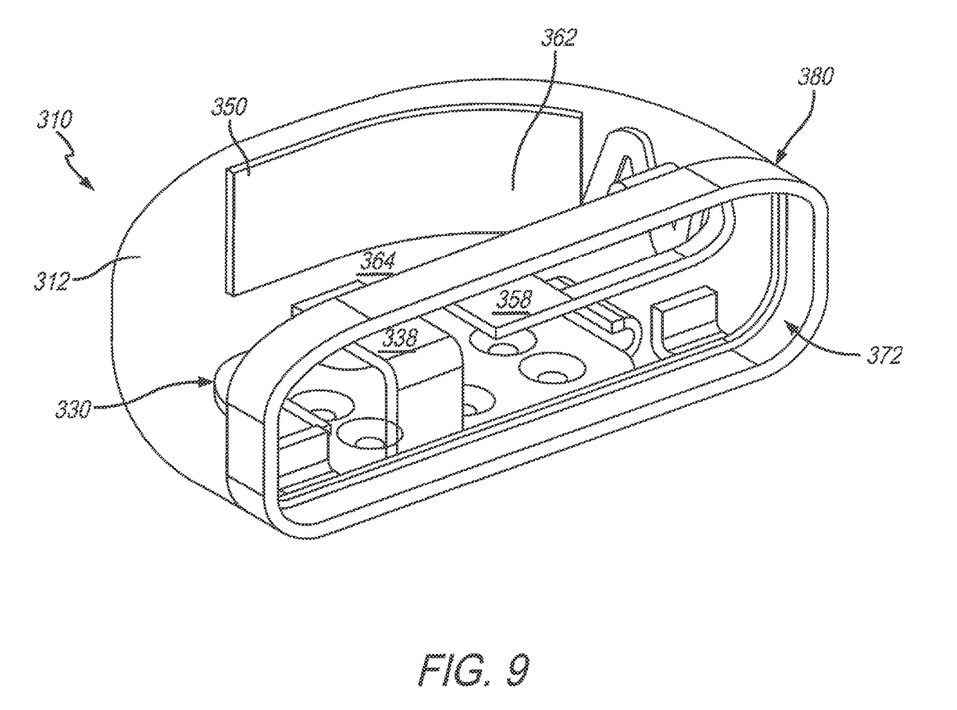
FIG. 9 illustrates a bottom perspective view of a header formed in accordance with an alternative embodiment.

FIG. 9 illustrates a bottom perspective view of a header 310 formed in accordance with an alternative embodiment. The header 310 includes a header body 312 with the same general overall structure as described above in connection with FIGS. 1-8B. For example the header 310 includes an antenna 350, and a sensing electrode 330. The header body 312 includes a window 362 that afford access to an interconnect cavity 364, where the sensor and antenna interconnect regions 338 and 358 are positioned.

In the embodiment of FIG. 9, a band 380 is provided about a perimeter of the recessed chamber 372. The band 380 may be formed with or adhesive layer secured to the header body 312 during the header preassembly operations of FIG. 7B. The band 380 includes one or more tabs 382 that are bent to extend inward above the recessed chamber 372 to provide mechanical anchoring points between the header 310 and the device housing.

While the foregoing examples described particular embodiments for the shapes of the various components, it is recognized that the components of the header and device may be modified. For example, more than one sensor electrode may be utilized and positioned in various locations within the header. More than one antenna may be utilized and positioned in a different position and orientation within the header. The shapes and overall constructions of the electrode and antenna may be varied. The overall shape of the header may be varied depending upon the desired shape of the overall device and the application for which the device is intended.

Figure 10:
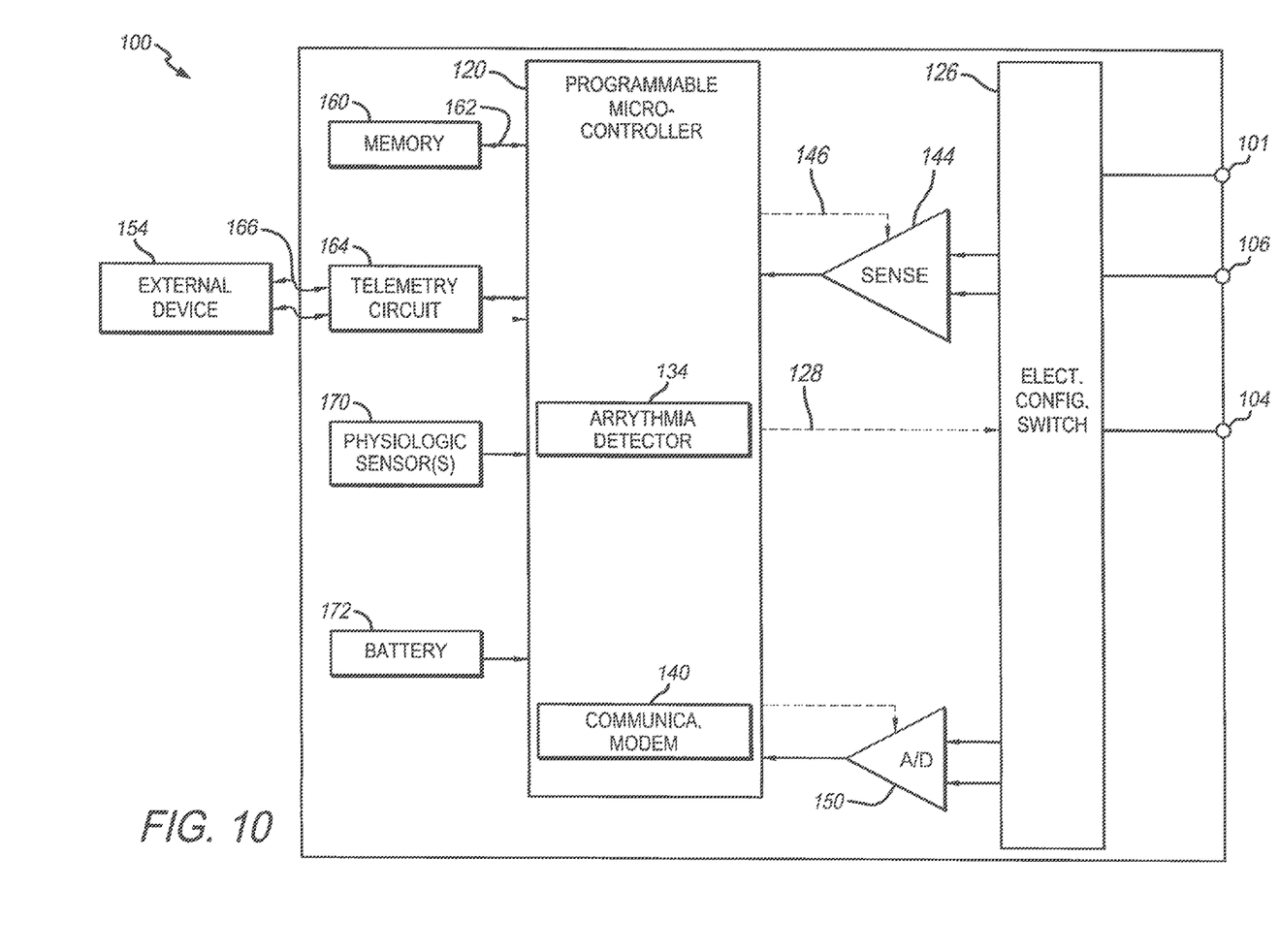
FIG. 10 illustrates shows a block diagram of an exemplary ICM device that is configured to be implanted into the patient in accordance with embodiments herein.

FIG. 10 illustrates shows a block diagram of an exemplary ICM device 100 that is configured to be implanted into the patient. Optionally, the ICM device 100 may be provided as an external device that is worn, held or otherwise located proximate to the patient during operation. The ICM device 100 may be implemented to monitor ventricular activity alone, or both ventricular and atrial activity through sensing circuitry. The ICM device 100 has a housing 101 to hold the electronic/computing components. The housing 101 (which is often referred to as the "can", "case", "encasing", or "case electrode") may be programmably selected to act as an electrode for certain sensing modes. Housing 101 further includes a connector (not shown) with at least one terminal 106 and preferably a second terminal 104. The terminals 106, 104 may be coupled to sensing electrodes (on the device housing, in the header, or located otherwise) that are provided upon or immediately adjacent the housing 101. Additionally or alternatively, the terminals 106, 104 may be connected to one or more leads having one or more electrodes provided thereon, where the electrodes are located in various locations about the heart. The type and location of each electrode may vary.

The ICM device 100 is configured to be placed subcutaneously utilizing a minimally invasive approach. Subcutaneous electrodes are provided on the housing 101 to simplify the implant procedure and eliminate a need for a transvenous lead system. The sensing electrodes may be located on opposite sides/ends of the device and designed to provide robust episode detection through consistent contact at a sensor-tissue interface. The ICM device 100 may be configured to be activated by the patient or automatically activated, in connection with recording subcutaneous ECG signals.

The ICM device 100 includes a programmable microcontroller 120 that controls various operations of the ICM device 100, including cardiac monitoring. Microcontroller 120 includes a microprocessor (or equivalent control circuitry), RAM and/or ROM memory, logic and timing circuitry, state machine circuitry, and I/O circuitry. The microcontroller 120 also performs the operations in connection with collecting cardiac activity data and analyzing the cardiac activity data to identify episodes of interest. Microcontroller 120 includes an arrhythmia detector 134 that is configured to analyze cardiac activity data to identify potential AF episodes as well as other arrhythmias (e.g. Tachycardias, Bradycardias, Asystole, etc.).

A switch 126 is optionally provided to allow selection of different electrode configurations under the control of the microcontroller 120. The switch 126 is controlled by a control signal 128 from the microcontroller 120. Optionally, the switch 126 may be omitted and the I/O circuits directly connected to the housing electrode and a second electrode.

The ICM device 100 is further equipped with a telemetry circuit 164 and a communication modem (modulator/demodulator) 140 to enable wireless communication. In one implementation, the telemetry circuit 164 and communication modem 140 use high frequency modulation, for example using RF or Blue Tooth telemetry protocols. The telemetry circuit 164 may include one or more transceivers. For example, the telemetry circuit 164 may be coupled to an antenna in the header that transmits communications signals in a high frequency range that will travel through the body tissue in fluids without stimulating the heart or being felt by the patient. The communication modem 140 may be implemented in hardware as part of the microcontroller 120, or as software/firmware instructions programmed into and executed by the microcontroller 120.

The ICM device 100 includes sensing circuitry 144 selectively coupled to one or more electrodes that perform sensing operations, through the switch 126 to detect cardiac activity data indicative of cardiac activity. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. In one embodiment, switch 126 may be used to determine the sensing polarity of the cardiac signal by selectively closing the appropriate switches.

The output of the sensing circuitry 144 is connected to the microcontroller 120 which, in turn, determines when to store the cardiac activity data (digitized by the ND data acquisition system 150) in the memory 160. The sensing circuitry 144 receives a control signal 146 from the microcontroller 120 for purposes of controlling the gain, threshold, polarization charge removal circuitry (not shown), and the timing of any blocking circuitry (not shown) coupled to the inputs of the sensing circuitry.

By way of example, the external device 154 may represent a bedside monitor installed in a patient's home and utilized to communicate with the ICM device 100 while the patient is at home, in bed or asleep. The external device 154 may be a programmer used in the clinic to interrogate the device, retrieve data and program detection criteria and other features. The external device 154 may be a device that can be coupled over a network (e.g. the Internet) to a remote monitoring service, medical network and the like. The external device 154 facilitates access by physicians to patient data as well as permitting the physician to review real-time ECG signals while being collected by the ICM device 100.

The microcontroller 120 is coupled to a memory 160 by a suitable data/address bus 162. The programmable operating parameters used by the microcontroller 120 are stored in memory 160 and used to customize the operation of the ICM device 100 to suit the needs of a particular patient. Such operating parameters define, for example, detection rate thresholds, sensitivity, automatic features, arrhythmia detection criteria, activity sensing or other physiological sensors, and electrode polarity, etc. The operating parameters of the ICM device 100 may be non-invasively programmed into the memory 160 through a telemetry circuit 164 in telemetric communication via communication link 166 with the external device 154. The telemetry circuit 164 allows intracardiac electrograms and status information relating to the operation of the ICM device 100 (as contained in the microcontroller 120 or memory 160) to be sent to the external device 154 through the established communication link 166.

The ICM device 100 may further include magnet detection circuitry (not shown), coupled to the microcontroller 120, to detect when a magnet is placed over the unit. A magnet may be used by a clinician to perform various test functions of the unit 100 and/or to signal the microcontroller 120 that the external device 154 is in place to receive or transmit data to the microcontroller 120 through the telemetry circuits 164.

The ICM device 100 can further include one or more physiologic sensor 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 120 for analysis and optional storage in the memory 160 in connection with the cardiac activity data, markers, episode information and the like. While shown as being included within the device 100, the physiologic sensor(s) 170 may be external to the device 100, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM device 100. The battery 172 is capable of operating at low current drains for long periods of time. The battery 172 also desirably has a predictable discharge characteristic so that elective replacement time can be detected. As one example, the device 100 employs lithium/silver vanadium oxide batteries. The battery 172 may afford various periods of longevity (e.g. three years or more of device monitoring). In alternate embodiments, the batter 172 could be rechargeable. See for example, U.S. Pat. No. 7,294,108, Cardiac event microrecorder and method for implanting same, which is hereby incorporated by reference.

The various methods as illustrated in the FIGS. and described herein represent exemplary embodiments of methods. The methods may be implemented in software, hardware, or a combination thereof, in various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

The specification and drawings are, accordingly, to be regarded in an illustrative rather than a restrictive sense, it will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown In the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of Items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 § 112(f), unless and until such claim limitations expressly use the phrase "means for" followed by a statement of function void of further structure.

What is claimed is:

1. An implantable cardiac device, comprising:
   a device housing having electronic components therein;
   a feed-through assembly joined to the device housing, the feed-through assembly including conductors having distal ends connected to the electronic components and having proximal ends projecting from the feed-through assembly;
   a header having a header body formed from a biocompatible material that encapsulates a sensing electrode and an antenna in the material forming the header body, the electrode and antenna including corresponding interconnect regions, the header body including a housing mounting surface that includes at least one passage aligned with the interconnection regions, the header body further including a window opening laterally onto a side of the header body, the window exposing the interconnect regions;
   the proximal ends of the conductors extending through the passage and aligning with the interconnection regions; and
   the window configured to provide access to the proximal ends and the interconnection regions.

2. The device of claim 1, wherein the header body is formed of an injection molded flowable material that embeds the electrode and antenna therein.

3. The device of claim 1, wherein the header body includes a recessed chamber formed in the housing mounting surface, the header body further comprising a band provided about a perimeter of the recessed chamber.

4. The device of claim 3, wherein the band includes one or more tabs that are bent to extend inward above the recessed chamber to provide mechanical anchoring points between the header and the device housing.

5. The system of claim 1, wherein the electronic components are configured to record cardiac signals sensed by the sensing electrode.

6. The system of claim 1, wherein the header includes opposite sides that are elongated to extend along a longitudinal axis and the electrode includes a sensor body portion, the sensor body portion being positioned to face laterally proximate to one of the sides of the header, the sensor body portion being oriented along a plane that extends at a select angle relative to the longitudinal axis.

7. The system of claim 1, wherein the passage extends in a first direction from the mounting surface through the header and the window opens laterally in a second direction onto the side of the header.

8. The system of claim 1, wherein the header body includes an interconnect cavity joined to the at least one passage extending from the mounting surface, the proximal ends and the interconnection regions located in the interconnect cavity.

* * * * *